United States Patent [19]

Oda et al.

[11] 4,440,948

[45] * Apr. 3, 1984

[54] PROCESS FOR PREPARING METHACRYLIC ACID

[75] Inventors: Yoshio Oda; Keiichi Uchida; Takeshi Morimoto; Seisaku Kumai, all of Yokohama, Japan

[73] Assignee: Asahi Glass Company, Ltd., Tokyo, Japan

[ * ] Notice: The portion of the term of this patent subsequent to Dec. 21, 1993 has been disclaimed.

[21] Appl. No.: 725,671

[22] Filed: Sep. 22, 1976

Related U.S. Application Data

[63] Continuation-in-part of Ser. No. 563,472, Mar. 31, 1975, Pat. No. 3,998,877.

[30] Foreign Application Priority Data

| Apr. 2, 1974 [JP] | Japan | 49-36597 |
| Apr. 2, 1974 [JP] | Japan | 49-36598 |
| Jul. 2, 1974 [JP] | Japan | 49-74971 |

[51] Int. Cl.$^3$ .................... C07C 51/25; C07C 57/055

[52] U.S. Cl. ................... 562/532; 562/534; 562/535; 562/536; 502/209; 502/211

[58] Field of Search ............ 260/530 N; 252/435, 252/437; 562/532, 534, 535

[56] References Cited

U.S. PATENT DOCUMENTS

| 3,875,220 | 4/1975 | White et al. | 260/530 N |
| 3,925,464 | 12/1975 | Oda et al. | 260/530 N |
| 3,976,688 | 8/1976 | Akiyama et al. | 260/530 N |
| 4,075,244 | 2/1978 | Akiyama et al. | 562/535 |

*Primary Examiner*—Vivian Garner
*Attorney, Agent, or Firm*—Oblon, Fisher, Spivak, McClelland & Maier

[57] ABSTRACT

Methacrylic acid is prepared by reacting methacrolein with molecular oxygen in the vapor phase at a temperature of from 230° C. to 450° C. in the presence of a catalyst having the formula $Mo_{12}P_{\alpha'}X_{\beta'}Y_{\gamma'}O_{\delta'}$ wherein X is at least one member of the group consisting of Cs and Tl; Y is at least one member of the group consisting of Cs and Tl; Y is at least one member of the group consisting of V, Zr, Nb, Ni, Ta and Fe; $\alpha'=0.1-3$; $\beta'=0.2-9$; $\gamma'=0.1-7$; $\delta'=36-100$.

12 Claims, No Drawings

PROCESS FOR PREPARING METHACRYLIC ACID

CROSS-REFERENCE TO RELATED APPLICATIONS

This application is a continuation-in-part of 563,472 filed Mar. 31, 1975, now U.S. Pat. No. 3,998,877, issued Dec. 21, 1976.

BACKGROUND OF THE INVENTION

1. Field of the Invention

This invention relates to a process for preparing methacrylic acid by the catalytic vapor phase oxidation of methacrolein characterized mainly by the use of novel catalysts.

2. Description of the Prior Art

Many catalysts have already been proposed which are useful for the preparation of unsaturated carboxylic acids having from three to four carbon atoms by the catalytic vapor phase oxidation of the corresponding unsaturated aldehydes with molecular oxygen. Some of these are excellent for preparing acrylic acid from acrolein and have been used for the production of acrylic acid on a large scale. Various catalysts for preparing methacrylic acid from methacrolein have also been prepared. However, methacrylic acid has not been produced commercially from methacrolein by use of these catalysts because of the low yield and/or the relatively short lifetime of the catalysts. The former defect occurs because methacrolein has relatively high activity compound to acrolein. Consequently, in the oxidation condition, it is more readily subject to complete oxidation to carbon monoxide and carbon dioxide rather than to partial oxidation to the desired product, whereby the yield of the product is low and the development of an appropriate catalyst is difficult. As a result it would be highly desirable to produce a catalyst mixture for commercially preparing methacrylic acid.

SUMMARY OF THE INVENTION

Accordingly, it is one object of this invention to provide a process for preparing methacrylic acid from methacrolein in high yields so as to enable commercial production thereof.

Briefly, this and other objects of the present invention as hereinafter will become apparent from the discussion below have been attained by a process for preparing methacrylic acid by the oxidation of methacrolein with molecular oxygen in the vapor phase in the presence of a catalyst consisting essentially of (a) molybdenum, (b) phosphorus, (c) at least one element selected from the group consisting of thallium and cesium, (d) at least one element selected from the group consisting of vanadium, zirconium, tin, niobium, nickel, tantalum and iron, and (e) oxygen.

DETAILED DESCRIPTION OF THE PREFERRED EMBODIMENTS

The catalysts of the present invention possess the desired catalytic activity and long life only when they contain all of the essential components. If the catalysts lack one or more of the essential components, the catalyst activity is very low. This results in small amounts of product methacrylic acid and short lifetime for the catalysts. Thus, catalysts other than those of the above mentioned combination are unsatisfactory for commercial applications. When the catalysts of this invention contain all of the essential components, they have very good catalytic activity and long lives.

The preferred catalysts of the invention are characterized by an empirical formula which in part contains 12 molybdenum atoms as follows:

$$Mo_{12}P_\alpha X_\beta Y_\gamma O_\delta \qquad (1)$$

wherein X is thallium and/or cesium; Y is vanadium, zirconium, tin, niobium, nickel, tantalum and/or iron; $\alpha$ is a number from 0.1 to 3; $\beta$ is a number from 0.1 to 7; $\gamma$ is a number from 0.1 to 7; and $\delta$ is determined by the oxidation states of the other elements. In addition to the essential components described above, the catalysts of the invention may contain at least one element selected from the group consisting of tungsten, cobalt, indium, manganese, cadmium, barium and selenium. Thus, the activity of the catalyst is further improved. When the catalyst of the invention contains the optional components above, the preferred empirical formula may be expressed as follows:

$$Mo_{12}P_\alpha X_\beta Y_\gamma Z_\epsilon O_\delta \qquad (2)$$

wherein X is at least one element selected from Tl and Cs; Y is at least one element selected from V, Zr, Sn, Nb, Ni, Ta and Fe; Z is at least one selected from W, Co, In, Mn, Cd, Ba and Se; $\alpha$ is a number from 0.1 to 3; $\beta$ is a number from 0.1 to 9; $\gamma$ is a number from 0.1 to 7; $\epsilon$ is a number from 0.1 to 7; $\delta$ is determined by the oxidation state of the other elements. Preferred embodiments of the catalyst may be expressed by the following formulas:

$$Mo_{12}P_{\alpha'}Cs_{\beta'}Sn_{\gamma'}O_{\delta'} \qquad (3)$$

wherein $\alpha'=0.1-3$; $\beta'=0.2-9$; $\gamma'=0.1-7$; $\delta'$—about 36—100; in the highest oxidation states of elements, preferably, $\alpha'=0.5-5$; $\beta'=0.5-5$; $\gamma'=0.3-5$.

$$Mo_{12}P_{\alpha'}Cs_{\beta'}Sn_{\gamma'}Z'_{\epsilon'}O_{\delta'} \qquad (4)$$

wherein $\alpha'$, $\beta'$ and $\gamma'$ are defined above, and Z' is selected from Ni, Co, Fe, V, Nb, Ta, Se, W and In; $\epsilon'=0.1-7$ preferably 0.3—5; $\delta'$ is determined by the oxidation state of the other elements and is about 36—130 when the elements are in their highest oxidation states.

$$Mo_{12}P_{\alpha'}Cs_{\beta'}V_{\gamma'}O_\delta \qquad (5)$$

wherein $\alpha'$, $\beta'$, $\gamma'$ and $\delta$ are defined above.

$$Mo_{12}P_{\alpha'}Cs_{\beta'}V_{\gamma'}Z''_{\epsilon'}O_{\delta'} \qquad (6)$$

wherein Z" is selected from W, Zr, Co, Ni, Se, Fe, Ba, In, Nb and Ta; and $\alpha$, $\beta'$, $\gamma'$, $\epsilon'$ and $\delta'$ are defined above.

$$Mo_{12}P_{\alpha'}Tl_{\beta'}Y'_{\gamma'}O_{\delta'} \qquad (7)$$

wherein Y' is at least one element selected from the group consisting of Zr, Ni, Nb, Ta, Ba and In; and $\alpha'$, $\beta'$, $\gamma'$ and $\delta'$ are defined above.

$$Mo_{12}P_{\alpha'}Tl_{\beta'}Y'_{\gamma'}Z'''_{\epsilon'}O_{\delta'} \qquad (8)$$

wherein Z''' is at least one element selected from the group consisting of Fe, V, Se and Sn; and $\alpha'$, $\beta'$, $\gamma'$, $\epsilon'$ and $\delta'$ are defined above. Suitable sources of starting materials of each component for use in the preparation of the catalysts include: For molybdenum-ortho, meta, or paramolybdic acid, ortho, meta or paramolybdates, heteropolymolybdic acid, heteropolymolybdates, molybdenum oxide and the like; For phosphorus-phosphoric acid, phosphates, polyphosphoric acid, polyphosphates and the like. Phosphomolybdic acid or phosphomolybdates may effectively be used as a common starting material for both the molybdenum and the phosphorus compounds. For cesium—cesium nitrate, cesium carbonate, cesium chloride and the like; For thallium—thallium nitrate, thallium carbonate and the like; For tin—stannous chloride, stannic chloride, stannic oxide and the like; For vanadium—vanadium pentaoxide, ammonium methavanadate and the like; For tungsten—tungsten trioxide, tungstic acid, salts of tungstic acids and the like; For indium—indium oxide, indium nitrate and the like; For niobium—niobium oxide, niobium hydroxide, niobium oxalate and the like; For tantalum—tantalum pentaoxide and the like; For selenium—selenic acid, selenious acid, selenium oxide and the like; For iron—ferric nitrate, ferric oxide, ferric chloride and the like; For cobalt—cobalt nitrate, cobaltic oxide and the like; For nickel—nickel nitrate, nickel chloride, nickel oxide and the like; For zirconium—zirconium oxide, zirconil nitrate and the like; and for barium—barium oxide, barium nitrate and the like.

The catalysts of the invention may be prepared from the sources of the above-mentioned elements by various methods, such as the concentrating-drying method or the coprecipitation method.

The catalysts of the invention are preferably prepared by the following methods. In the preparation of the catalysts, phosphomolybdic acid or the components for forming phosphomolybdic acid under the condition of the following reaction with the source of cesium or thallium are used as the sources of molybdenum and phosphorus. The use of phosphomolybdic acid is preferable because it is easily available and excellent catalysts are obtained.

When ammonium phosphomolybdate is used as the sources of molybdenum and phosphorus, the catalytic properties are remarkably inferior, though it is a similar material. The components for forming phosphomolybdic acid under the above-mentioned reaction condition are preferably mixtures of o-, m- or p-molybdic acid and phosphoric acid or a polyphosphoric acid.

The source of cesium or thallium which is a water soluble cesium or thallium compound is used for the reaction with phosphomolybdic acid or the components for forming phosphomolybdic acid. Suitable sources of cesium or thallium include nitrates, carbonates and hydrochlorides of cesium or thallium.

The reaction of phosphomolybdic acid with the source of cesium or thallium is carried out in an aqueous solution by uniformly mixing them to form a slurry. The reaction is easily performed. In order to promote the reaction to obtain the catalyst having higher catalytic properties, the slurry is preferably aged in an acidic condition especially at a pH of lower than 4, at 60° to 110° C. for 3 to 6 hours.

The resulting reaction mixture was admixed with at least one of sources V, Zr, Ni, Nb, Ta and Fe and if desired at least one of sources of W, Co. Ba, Se and In.

These sources need not to be water soluble and can be water insoluble. The important feature is to admix them with the reaction mixture of phosphomolybdic acid and the source of cesium or thallium. When they are directly admixed with phosphomolybdic acid without reacting phosphomolybdic acid with the source of cesium or thallium, the catalytic properties are remarkably low.

The reaction of phosphomolybdic acid with the source of cesium or thallium is relatively fast. Accordingly, it is possible to simultaneously contact the source of cesium or thallium and the other sources with phosphomolybdic acid besides they predominantly suppress the reaction. Suitable sources of Zr, Ni, Nb, Ta, In, Fe, V, W, Ba, Se and Co include oxides, chlorides, sulfates and nitrates thereof.

These sources are admixed with the slurry after ageing it. When these sources are water insoluble as oxides thereof, these sources can be added to the slurry before ageing.

The slurry is aged and the medium is concentrated or dried by the vaporization and the product is preferably calcined at 150° to 500° C. especially 200° to 450° C. for about 1 to 48 hours. The resulting catalyst of the invention has preferably a specific surface area of 0.01 to 50 $m^2/g$.

The reason why the catalyst has excellent catalytic properties, is not clear. According to X-ray diffraction of the catalyst, the fine structure of the catalyst is different from those of catalysts prepared by the other methods. The catalytic properties of the catalyst are remarkably superior to the other types or the same types prepared by the other methods.

The structure of the catalyst may be a homogeneous mixture of the oxides of all the components, or a compound or complex formed by means of the mutual reaction of the salts of molybdenum and phosphorus with the oxides of the other components. In particular, it is found that when the catalyst has a structure composed of cesium or thallium phosphomolybdate, it has superior catalytic activity and a longer life than conventional catalysts.

In order to reduce cost and to improve the physical properties of the catalysts, they are preferably supported on a carrier. Suitable substrates include silica, silica containing materials, titania, alumina, silicon carbide and the like. It is preferred to use a carrier having a relatively large pore radius. The amount of the carrier used is preferably in the range of 30–97% by weight based on the supported catalyst. The catalyst can be supported on the carrier by the conventional dipping or blending methods.

In the preparation of methacrylic acid from methacrolein, the reaction temperature may vary from 230° to 450° C., preferably 250° to 380° C. The reaction pressure may vary from 0.5 to 40 atmospheres absolute, preferably from about 1 to 10 atmospheres absolute. When the reaction pressure is at the high end of the indicated range, the reaction temperature may be somewhat lower within the indicated range. Contact time for the reactants and the catalyst usually varies from 0.2 to 30 seconds preferably 1 to 20 seconds. The molecular ratio of oxygen to methacrolein in the feed gas usually varies from 1:10 to 10:1, preferably from 1:3 to 3:1. Suitable sources of oxygen include those which introduce molecular oxygen into the reaction. Air is preferred because of its economy. Steam may be added to the gaseous reaction mixture thereby improving the yield of methacrylic acid. The concentration of the steam may vary from 2 to 80% preferably from 10 to 50% of the volume of the feed. In addition, nitrogen, saturated hydrocarbons such as methane, ethane, propane, butane and the like or other inert gases may also be added to the gaseous mixture. Suitable reactors for the vapor phase oxidation reaction include a fixed-bed type reactor and a fluidized-bed type reactor and the like. The operation can be continuous or batch. The methacrylic acid may be recovered from the reaction products by any conventional method. Suitable separate techniques include condensation and/or extraction followed by distillation.

In accordance with the process of the invention, the industrial production of methacrylic acid from methacrolein is advantageously attained. This in turn enables industrial production of methacrylate (MMA) which is produced from methacrylic acid, without the need for employment of conventional processes such as the cyanohydrin method which possess several drawbacks, e.g., pollution effects.

Having generally described the invention, a more complete understanding can be obtained by reference to certain specific examples, which are intended for purposes of illustration only and are not intended to be limiting unless otherwise specified.

The following definitions are used in the Examples for the conversion percentage of acetic acid:

$$\text{Conversion \%} = \frac{\text{total reacted methacrolein (moles)}}{\text{methacrolein in the feed (moles)}} \times 100$$

$$\text{Selectivity of methacrylic acid (\%)} = \frac{\text{methacrylic acid in the effluent (moles)}}{\text{total reacted methacrolein (moles)}} \times 100$$

$$\text{Selectivity of acetic acid (\%)} = \frac{\text{acetic acid in the effluent (moles)}}{\text{total reacted methacrolein (moles)}} \times 100 \times \tfrac{1}{2}$$

EXAMPLE 1

A solution of 13.4 g of thallium nitrate and 2.0 g of ammonium nitrate in 50 cc of water was added with stirring to a solution of 58 g of phosphomolybdic acid dissolved in 50 cc of water. A 3.0 g sample of zirconium oxide was added to the resulting solution. The mixture was heated with stirring to form a slurry. The slurry was concentrated and dried at 120° C. for 12 hours and the dried product was calcined at 420° C. for 6 hours to yield a solid having the atomic ratio values corresponding to the formula $Mo_{12}P_1Tl_2Zr_1O_{42}$. The solid was passed through a sieve to yield catalyst particles of 35–100 mesh. A U-shaped reactor made of stainless steel having an inner diameter of 8 mm was filled with the catalyst particles. A gaseous mixture composed of 4% of methacrolein; 10% of oxygen; 30% of steam and 56% of nitrogen (percent by volume) was passed through the reactor with a contact time of 4 seconds at 340° C. The following results were obtained.

| Conversion of methacrolein (%) | 86% |
|---|---|
| Selectivity to methacrylic acid (%) | 71% |
| Selectivity to acetic acid (%) | 7% |

EXAMPLES 2–21

Catalysts were prepared in accordance with the process of Example 1, except that 3.3 g of niobium pentoxide; 3.6 g of nickel nitrate; 3.8 g of barium oxide; 8.8 g of indium nitrate or various combinations of these were alternately used instead of zirconium oxide, yielding solids having the atomic ratio values shown by the formulas in Table 1. The reaction of Example 1 was repeated using these catalysts. The results are also shown in Table 1.

TABLE 1

| Example No. | Catalysts | Methacrolein conversion (%) | Methacrylic acid selectivity (%) | Acetic acid selectivity (%) |
|---|---|---|---|---|
| 2  | $Tl_2Mo_{12}Nb_1P_1O_{43}$ | 70 | 75 | 4 |
| 3  | $Tl_2Mo_{12}Ni_1P_1O_{41}$ | 65 | 71 | 3 |
| 4  | $Tl_2Mo_{12}In_1P_1O_{42}$ | 90 | 78 | 2 |
| 5  | $Tl_2Mo_{12}Zr_1Nb_1P_1O_{45}$ | 77 | 78 | 9 |
| 6  | $Tl_2Mo_{12}Zr_1Ni_1P_1O_{43}$ | 71 | 79 | 4 |
| 7  | $Tl_2Mo_{12}Zr_1In_1P_1O_{44}$ | 65 | 79 | 8 |
| 8  | $Tl_2Mo_{12}Nb_1Ni_1P_1O_{44}$ | 77 | 77 | 7 |
| 9  | $Tl_2Mo_{12}Nb_1In_1P_1O_{44}$ | 97 | 68 | 6 |
| 10 | $Tl_2Mo_{12}In_1Ni_1P_1O_{43}$ | 81 | 71 | 5 |
| 11 | $Tl_2Mo_{12}Ba_1Zr_1P_1O_{43}$ | 86 | 80 | 10 |
| 12 | $Tl_2Mo_{12}Ba_1Nb_1P_1O_{44}$ | 73 | 71 | 6 |
| 13 | $Tl_2Mo_{12}Ba_1Ni_1P_1O_{42}$ | 73 | 82 | 7 |
| 14 | $Tl_2Mo_{12}Ba_1In_1P_1O_{43}$ | 90 | 65 | 14 |
| 15 | $Tl_2Mo_{12}Ba_1P_1O_{41}$ | 84 | 73 | 9 |
| 16 | $Tl_2Mo_{12}Zr_3P_1O_{46}$ | 70 | 65 | 7 |
| 17 | $Tl_7Mo_{12}Nb_1P_1O_{45}$ | 59 | 60 | 5 |
| 18 | $Tl_2Mo_{12}Zr_1Ni_5P_1O_{47}$ | 63 | 63 | 4 |
| 19 | $Tl_2Mo_{12}Nb_1In_3P_2O_{47}$ | 71 | 55 | 9 |
| 20 | $Tl_1Mo_{12}Ba_2Zr_1P_{0.5}O_{42}$ | 76 | 70 | 5 |
| 21 | $Tl_2Mo_{12}Ba_{0.5}In_{0.5}P_1O_{41}$ | 80 | 60 | 7 |

EXAMPLE 22

A solution of 13.4 g of thallium nitrate and 2.0 g of ammonium nitrate in 50 cc of water was added with stirring to a solution of 58 g of phosphomolybdic acid dissolved in 50 cc of water. A 3.0 g sample of zirconium oxide and 10.2 g of ferric nitrate were added to the resulting solution, and the mixture was heated with stirring to form a slurry. The slurry was concentrated and dried at 120° C. for 12 hours and the dried product was calcined at 420° C. for 6 hours to yield a solid having the atomic ratio values corresponding to the formula $Mo_{12}P_1Tl_2Zr_1Fe_1O_{44}$. The solid was passed through a sieve to yield catalyst particles of 35–100 mesh. A U-shaped reactor made of stainless steel having an inner diameter of 8 mm was filled with the catalyst particles. The reaction of Example 1 was repeated using these catalysts. The following results were obtained.

| Conversion of methacrolein (%) | 74% |
|---|---|
| Selectivity to methacrylic acid (%) | 76% |
| Selectivity to acetic acid (%) | 7% |

EXAMPLES 23–42

Catalysts were prepared in accordance with the process of Example 37 except that 3.3 g of niobium pentaoxide; 3.6 g of nickel nitrate or 8.8 g of indium nitrate were alternately used instead of zirconium oxide; or that 3.0 g of ammonium metavanadate; 3.8 g of barium oxide; 3.2 g of selenious acid or 3.8 g of tin oxide instead of ferric nitrate, yielding solids having the atomic ratio values shown by the formulas in Table 2. The reaction of Example 22 was repeated using these catalysts. The results are also shown in Table 2.

EXAMPLE 43

A solution of 9.8 g of cesium nitrate and 2.0 g of ammonium nitrate in 50 cc of water was added with stirring to a solution of 58 g of phosphomolybdic acid dissolved in 50 cc of water. A solution of 3.0 g of ammonium metavanadate in 100 cc of water was added to the resulting solution. The mixture was heated with stirring to form a slurry. The slurry was concentrated and dried at 120° C. for 12 hours and the dried product was calcined at 420° C. to yield a solid having the atomic ratio values corresponding to the formula $Mo_{12}P_1Cs_2V_1O_{43}$. The solid was passed through a sieve to yield catalyst particles of 35–100 mesh.

TABLE 2

| Example No. | Catalysts | Methacrolein conversion (%) | Methacrylic acid selectivity (%) | Acetic acid selectivity (%) |
|---|---|---|---|---|
| 23 | $Tl_2Mo_{12}Zr_1V_1P_1O_{45}$ | 83 | 72 | 7 |
| 24 | $Tl_2Mo_{12}Zr_1Se_1P_1O_{44}$ | 66 | 85 | 4 |
| 25 | $Tl_2Mo_{12}Zr_1Sn_1P_1O_{44}$ | 60 | 83 | 5 |
| 26 | $Tl_2Mo_{12}Nb_1Fe_1P_1O_{44}$ | 78 | 84 | 9 |
| 27 | $Tl_2Mo_{12}Nb_1V_1P_1O_{45}$ | 86 | 78 | 7 |
| 28 | $Tl_2Mo_{12}Nb_1Se_1P_1O_{45}$ | 89 | 75 | 8 |
| 29 | $Tl_2Mo_{12}Nb_1Sn_1P_1O_{45}$ | 77 | 79 | 10 |
| 30 | $Tl_2Mo_{12}Ni_1Fe_1P_1O_{43}$ | 87 | 73 | 11 |
| 31 | $Tl_2Mo_{12}Ni_1V_1P_1O_{44}$ | 70 | 76 | 3 |
| 32 | $Tl_2Mo_{12}Ni_1Se_1P_1O_{43}$ | 78 | 77 | 5 |
| 33 | $Tl_2Mo_{12}Ni_1Sn_1P_1O_{43}$ | 91 | 71 | 5 |
| 34 | $Tl_2Mo_{12}In_1Fe_1P_1O_{43}$ | 75 | 74 | 13 |
| 35 | $Tl_2Mo_{12}In_1V_1P_1O_{44}$ | 74 | 72 | 8 |
| 36 | $Tl_2Mo_{12}In_1Se_1P_1O_{44}$ | 84 | 77 | 10 |
| 37 | $Tl_2Mo_{12}In_1Sn_1P_1O_{44}$ | 95 | 81 | 7 |
| 38 | $Mo_{12}P_1Tl_5Zr_1V_1O_{46}$ | 63 | 57 | 5 |
| 39 | $Mo_{12}P_3Tl_2Nb_1V_1O_{50}$ | 66 | 82 | 7 |
| 40 | $Mo_{12}P_1Tl_2Ni_1Fe_3O_{46}$ | 82 | 63 | 10 |
| 41 | $Mo_{12}P_1Tl_2In_5Fe_1O_{49}$ | 71 | 64 | 13 |
| 42 | $Mo_{12}P_1Tl_2In_1Sn_5O_{52}$ | 85 | 72 | 5 |

A U-shaped reactor made of stainless steel having an inner diameter of 8 mm was filled with the catalyst particles. A gaseous mixture composed of 4% of methacrolein; 10% of oxygen; 30% of steam and 56% of nitrogen (percent by volume) was passed through the reactor with the contact time of 4 seconds, at 340° C. for 4 hours. The following results were obtained.

| | |
|---|---|
| Conversion of methacrolein (%) | 65% |
| Selectivity to methacrylic acid (%) | 75% |
| Selectivity to acetic acid (%) | 4% |

EXAMPLE 44

A solution of 9.8 g of cesium nitrate and 2.0 g of ammonium nitrate in 50 cc of water was added with stirring to a solution of 58 g of phosphomolybdic acid dissolved in 50 cc of water. A solution of 3.0 g of ammonium metavanadate and 5.8 g of tungsten oxide in 100 cc of water was added to the resulting solution. The mixture was heated with stirring to form a slurry. The slurry was concentrated and the dried at 120° C. for 12 hours and the dried product was calcined at 420° C. to yield a solid having the atomic ratio values corresponding to the formula $Mo_{12}P_1Cs_2V_1W_1O_{46}$. The solid was passed through a sieve to yield catalyst particles of 35–100 mesh. A U-shaped reactor made of stainless steel having an inner diameter of 8 mm was filled with the catalyst particles. A gaseous mixture composed of 4% of methacrolein; 10% of oxygen; 30% of steam and 56% of nitrogen (percent by volume) was passed through the reactor with the contact time of 4 seconds, at 340° C. for 4 hours. The following results were obtained.

| | |
|---|---|
| Conversion of methacrolein (%) | 71% |
| Selectivity to methacrylic acid (%) | 77% |
| Selectivity to acetic acid (%) | 6% |

EXAMPLES 45–52

Catalysts were prepared in accordance with the process of Example 59, except that 3.0 g of zirconium oxide; 7.8 g of cobalt nitrate; 7.2 g of nickel nitrate; 3.2 g of selenious acid; 10.2 g of ferric nitrate; 8.8 g of indium nitrate; 3.3 g of niobium pentaoxide or 3.8 g of barium oxide were alternately used instead of tungsten oxide, producing solids having the atomic ratio values shown by the formulas in Table 3. The reaction of Example 44 was repeated using these catalysts. The results are also shown in Table 3.

TABLE 3

| Example No. | Catalysts | Methacrolein Conversion (%) | Methacrylic acid selectivity (%) | Acetic acid selectivity (%) |
|---|---|---|---|---|
| 45 | $Cs_2Mo_{12}V_1Zr_1P_1O_{45}$ | 76 | 79 | 8 |
| 46 | $Cs_2Mo_{12}V_1Co_1P_1O_{44}$ | 96 | 59 | 10 |
| 47 | $Cs_2Mo_{12}V_1Ni_1P_1O_{44}$ | 71 | 70 | 3 |
| 48 | $Cs_2Mo_{12}V_1Se_1P_1O_{45}$ | 75 | 69 | 5 |
| 49 | $Cs_2Mo_{12}V_1Fe_1P_1O_{44}$ | 96 | 66 | 11 |
| 50 | $Cs_2Mo_{12}V_1In_1P_1O_{44}$ | 100 | 57 | 15 |
| 51 | $Cs_2Mo_{12}V_1Nb_1P_1O_{44}$ | 87 | 71 | 6 |
| 52 | $Cs_2Mo_{12}V_1Ba_1P_1O_{44}$ | 75 | 80 | 5 |

EXAMPLES 53–58

Catalysts were prepared in accordance with the processes of Examples 43 and 44 except changing the amounts of the source materials for the metal components. The reaction of Examples 43 was repeated using these catalysts. The results are shown in Table 4.

TABLE 4

| Example No. | Catalysts | Methacrolein conversion (%) | Methacrylic acid selectivity (%) | Acetic acid selectivity (%) |
|---|---|---|---|---|
| 53 | $Mo_{12}P_{0.5}Cs_2V_1O_{41}$ | 72 | 67 | 4 |
| 54 | $Mo_{12}P_1Cs_7V_1Co_1O_{46}$ | 68 | 68 | 8 |
| 55 | $Mo_{12}P_1Cs_2V_5W_1O_{56}$ | 67 | 74 | 6 |
| 56 | $Mo_{12}P_2Cs_2V_1Fe_6O_{52}$ | 66 | 69 | 3 |
| 57 | $Mo_{12}P_{0.5}Cs_{0.5}V_{0.5}Nb_1O_{42}$ | 77 | 67 | 10 |
| 58 | $Mo_{12}P_1Cs_2V_1In_{0.5}O_{44}$ | 81 | 62 | 5 |

In order to study the structure of the catalysts of the examples, X-ray diffraction and infrared spectra analysis have been conducted. In all of the examples, the catalysts containing cesium had a structure composed of cesium phosphomolybdate. The catalysts containing thallium had a structure composed of thallium phosphomolybdate. In Example 1 and Examples 43, the reactions were continued for long periods (1, 60 and 120 days) in order to test the lifetime of the catalysts. The results are shown in Table 5 and Table 6.

TABLE 5

| Reaction time (days) | Reaction temperature (°C.) | Methacrolein conversion (%) | Methacrylic acid selectivity (%) | Acetic acid selectivity (%) |
|---|---|---|---|---|
| 1 | 340 | 86 | 71 | 7 |
| 60 | 340 | 85 | 72 | 8 |

TABLE 5-continued

| Reaction time (days) | Reaction temperature (°C.) | Methacrolein conversion (%) | Methacrylic acid selectivity (%) | Acetic acid selectivity (%) |
|---|---|---|---|---|
| 120 | 340 | 86 | 71 | 9 |

TABLE 8

| Reaction time (days) | Reaction temperature (°C.) | Methacrolein conversion (%) | Methacrylic acid selectivity (%) | Acetic acid selectivity (%) |
|---|---|---|---|---|
| 1 | 340 | 65 | 75 | 4 |
| 60 | 340 | 67 | 73 | 6 |
| 120 | 340 | 64 | 76 | 7 |

As is clear from the results, the lifetimes of the catalysts of the invention are long. That is, they maintain their catalytic activity for long periods of active use.

REFERENCE 1

In accordance with the process of Example 1 except that a mixture of ammonium paramolybdate, phosphoric acid and nitric acid which forms ammonium phosphomolybdate in the reaction condition, was used instead of phosphomolybdic acid, whereby a catalyst having the formula $Tl_2Mo_{12}Zr_1P_1O_x$ was obtained. The reaction of Example 1 was repeated using the catalyst, the following results were found.

| Conversion of methacrolein | 40% |
|---|---|
| Selectivity to methacrylic acid | 62% |
| Selectivity to acetic acid | 7% |

REFERENCE 2

In accordance with the process of Example 1 except that 58 g of phosphomolybdic acid was dissolved in 50 cc of water and a mixture of 5.6 g of zirconium oxide, 20 cc of nitric acid and 40 cc of water was admixed with the solution, whereby a catalyst having the formula $Tl_2Mo_{12}Zr_1P_1O_x$ was obtained. The reaction of Example 1 was repeated using the catalyst. The following results were found.

| Conversion of methacrolein | 32% |
|---|---|
| Selectivity to methacrylic acid | 65% |
| Selectivity to acetic acid | 9% |

REFERENCE 3

Catalysts were prepared in accordance with the process of Example 1, except that either no thallium nitrate or no zirconium oxide was used so as to yield a solid having the atomic ratio values corresponding to the formula $Mo_{12}P_1Zr_1O_{42}$ or $Mo_{12}P_1Tl_2O_{40}$. The reaction of Example 1 was repeated using these catalysts. The results are shown as follows.

| | $Mo_{12}P_1Zr_1O_{42}$ | $Mo_{12}P_1Tl_2O_{40}$ |
|---|---|---|
| Conversion of methacrolein (%) | 53% | 64% |
| Selectivity to methacrylic acid (%) | 27% | 35% |
| Selectivity to acetic acid (%) | 4% | 4% |

REFERENCE 4

In accordance with the process of Example 22 except that a mixture of ammonium paramolybdate, phosphoric acid and nitric acid was used instead of phosphomolybdic acid, whereby a catalyst having the formula of $Tl_2Mo_{12}Zr_1Fe_1P_1O_x$ was obtained. The reaction of Example 2 was repeated using the catalyst. The following results were found.

| Conversion of methacrolein | 44% |
|---|---|
| Selectivity to methacrylic acid | 65% |
| Selectivity to acetic acid | 11% |

REFERENCE 5

In accordance with the process of Example 22 except that a solution of 58 g of phosphomolybdic acid in 50 cc of water was admixed with a dispersion of 3.0 g of zirconium oxide in 40 cc of water, and then a solution of 10.2 g of ferric nitrate in 50 cc of water was added to the solution and then a solution of 13.4 g of thallium nitrate in 50 cc of water and a solution of 2.0 g of ammonium nitrate in 50 cc of water were added to the mixture whereby a catalyst having the formula of $Tl_2Mo_{12}Zr_1Fe_1P_1O_x$ was obtained. The reaction of Example 1 was repeated using the catalyst. The following results were found.

| Conversion of methacrolein | 51% |
|---|---|
| Selectivity to methacrylic acid | 60% |
| Selectivity to acetic acid | 7% |

REFERENCE 6

In accordance with the process of Example 43 except that a mixture of ammonium paramolybdate, phosphoric acid and nitric acid which forms ammonium phosphomolybdate in the reaction condition was used instead of phosphomolybdic acid, whereby a catalyst having the formula $Mo_{12}P_1Cs_2V_1Ox$ was obtained. The reaction of Example 1 was repeated using the catalyst. The following results were found.

| Conversion of methacrolein | 42% |
|---|---|
| Selectivity to methacrylic acid | 58% |
| Selectivity to acetic acid | 5% |

REFERENCE 7

In accordance with the process of Example 1 except that a solution of 58 g of phosphomolybdic acid in 50 cc of water was admixed with a solution of 3.0 g of ammonium metavanadate in 20 cc of nitric acid and 40 cc of water and then a solution of 9.8 g of cesium nitrate in 50 cc of water and a solution of 2.0 g of ammonium nitrate in 50 cc of water, whereby a catalyst having the formula $Mo_{12}P_1Cs_2V_1Ox$ was obtained. The reaction of Example 43 was repeated using the catalyst. The following results were found.

| | |
|---|---|
| Conversion of methacrolein | 32% |
| Selectivity to methacrylic acid | 65% |
| Selectivity to acetic acid | 9% |

REFERENCE 8

Catalysts were prepared in accordance with the process of Example 43, except that either no cesium nitrate or no ammonium metavanadate were used. Solids were produced having the atomic ratio values corresponding to the formulas: $Mo_{12}P_1V_1O_{43}$ or $Mo_{12}P_1Cs_2O_{40}$. The reaction of Example 43 was repeated using these catalysts. The results were as follows.

| | $Mo_{12}P_1V_1O_{43}$ | $Mo_{12}P_1Cs_2O_{40}$ |
|---|---|---|
| Conversion of methacrolein (%) | 47% | 42% |
| Selectivity to methacrylic acid (%) | 56% | 68% |
| Selectivity to acetic acid (%) | 7% | 8% |

REFERENCE 9

In accordance with the process of Example 44 except that a mixture of ammonium paramolybdate, phosphoric acid and nitric acid was used instead of phosphomolybdic acid whereby a catalyst having the formula $Mo_{12}P_1Cs_1V_1W_1O_x$ was obtained. The reaction of Example 2 was repeated using the catalyst. The following results were found.

| | |
|---|---|
| Conversion of methacrolein | 44% |
| Selectivity to methacrylic acid | 59% |
| Selectivity to acetic acid | 4% |

REFERENCE 10

In accordance with the process of Example 22 except that a solution of 5.8 g of phosphomolybdic acid in 50 cc of water was mixed with a dispersion of 3.0 g of ammonium metavanadate in 40 cc of water and then a solution of 5.8 g of tungsten oxide in 50 cc of water was added to the slurry and then a solution of 9.8 g of cesium nitrate in 50 cc of water and a solution of 2.0 g of ammonium nitrate in 50 cc of water were added to the mixture whereby a catalyst having the formula $MO_{12}P_1Cs_1V_1W_1O_x$ was obtained. The reaction of Example 44 was repeated using the catalyst. The following results were found.

| | |
|---|---|
| Conversion of methacrolein | 53% |
| Selectivity to methacrylic acid | 49% |
| Selectivity of acetic acid | 8% |

Having now fully described the invention, it will be apparent to one of ordinary skill in the art that many changes and modifications can be made thereto without departing from the spirit or scope of the invention as set forth herein.

What is claimed is:

1. A process for preparing methacrylic acid, which comprises:

reacting methacrolein with molecular oxygen in the vapor phase at a temperature of from 230° C. to 450° C. in the presence of a catalyst consisting essentially of $$Mo_{12}P_{\alpha'}X_{\beta'}Y_{\gamma'}O_{\delta'}$$

wherein X is at least one member selected from the group consisting of Cs and Tl; Y is at least one member selected from the group consisting of V, Zr, Nb, Ni, Ta and Fe; $\alpha'=0.1-3$; $\beta'=0.2-9$; $\gamma'=0.1-7$ and $\delta'=36-100$, which contains a cesium or thallium phosphomolybdate structural component.

2. The process of claim 1 wherein the reaction mixture of the cesium or thallium compound and phosphomolybdic acid or the components for forming phosphomolybdic acid under the reaction condition, is aged at a pH less than 4 at 60° to 110° C. for 3 to 6 hours.

3. The process of claim 1 wherein the specific surface area of the catalyst is in a range of 0.01 to 50 m²/g.

4. The process of claim 1 wherein the catalyst is supported by silica, titania, alumina or silicon carbide.

5. The process of claim 1, wherein the catalyst consists essentially of molybdenum, phosphorus, cesium, vanadium and oxygen.

6. The process of claim 1, wherein the reaction pressure is from 0.5 to 40 atmospheres absolute.

7. The process of claim 1, wherein the molecular ratio of the oxygen reactant is from 0.1 to 10 relative to the amount of methacrolein.

8. The process of claim 1, wherein steam present in a concentration of from 2 to 80% of the volume of the feed, is added to the reaction mixture.

9. The process of claim 1, wherein the catalyst is prepared by reacting a water soluble cesium or thallium compound with phosphomolybdic acid or phosphomolybdic acid prepared from mixtures of o-, m-, or p-molybdic acid and phosphoric acid or polyphosphoric acid, thereby forming said cesium or thallium phosphomolybdate structural component, and admixing the reaction mixture was at least one source of V, Zr, Nb, Ni, Ta and Fe, and concentrating and drying the mixture and calcining said mixture at 150° C. to 500° C.

10. A process for preparing methacrylic acid, which comprises:

reacting methacrolein with molecular oxygen in the vapor phase at a temperature of from 230° C. to 450° C. in the presence of a catalyst consisting essentially of $$Mo_{12}P_{\alpha'}Cs_{\beta'}V_{\gamma'}Z''_{\epsilon'}O_{\delta'}$$

wherein Z" is selected from the group consisting of W, Zr, Co, Ni, Se, Fe, Ba, In, Nb and Ta; $\alpha'$, $\beta'$, $\gamma'$, and $\delta'$ are as defined in claim 16 and $\epsilon'=0.1-7$, which contains a cesium phosphomolybdate structural component.

11. A process for preparing methacrylic acid, which comprises:

reacting methacrolein with molecular oxygen in the vapor phase at a temperature of from 230° C. to 450° C. in the presence of a catalyst consisting essentially of $$Mo_{12}P_{\alpha'}Tl_{\beta'}Y'_{\gamma'}O_{\delta'}$$

wherein Y' is at least one element selected from the group consisting of Zr, Ni, Nb, Ta, Ba and In; and $\alpha'$, $\beta'$, $\gamma'$ and $\delta'$ are as defined in claim 10, which contains a thallium phosphomolybdate structural component.

12. A process for preparing methacrylic acid, which comprises:

reacting methacrolein with molecular oxygen in the vapor phase at a temperature of from 230° C. to 450° C. in the presence of a catalyst consisting essentially of:

$$Mo_{12}P_{\alpha'}Tl_{\beta'}Y'_{\gamma'}Z'''_{\epsilon'}O_{\delta'}$$

wherein Y' is at least one element selected from the group consisting of Zr, Ni, Nb, Ta, Ba and In, Z''' is at least one element selected from the group consisting of Fe, V, Se and Sn and $\alpha'$, $\beta'$, $\gamma'$, $\epsilon'$, and $\delta'$ are as defined in claim 10, which contains a thallium phosphomolybdate structural component.

* * * * *